United States Patent [19]

Smith et al.

[11] Patent Number: 4,883,917
[45] Date of Patent: Nov. 28, 1989

[54] QUATERNARY AMMONIUM COMPOUNDS

[75] Inventors: Kim R. Smith; Joe D. Sauer; James E. Borland, all of Baton Rouge, La.

[73] Assignee: Ethyl Corporation, Richmond, Va.

[21] Appl. No.: 782,353

[22] Filed: Oct. 1, 1985

[51] Int. Cl.$^4$ ............................................. C07C 91/40
[52] U.S. Cl. .................................................. 564/292
[58] Field of Search ...................... 564/291, 292, 281; 556/417, 413; 560/155, 171, 250

[56] References Cited

U.S. PATENT DOCUMENTS

| | | | |
|---|---|---|---|
| 2,541,248 | 2/1951 | Hibbs | 167/22 |
| 3,054,678 | 9/1962 | Michener et al. | 99/150 |
| 4,401,577 | 8/1983 | Richmond | 564/291 X |
| 4,470,918 | 9/1984 | Mosier | 564/291 X |
| 4,480,126 | 10/1984 | Rutzen | 564/291 X |
| 4,675,118 | 6/1987 | Stanley et al. | 564/291 X |

FOREIGN PATENT DOCUMENTS 2711577 3/1977 Fed. Rep. of Germany ...... 564/292 UX

Primary Examiner—Paul F. Shaver
Attorney, Agent, or Firm—Joseph D. Odenweller

[57] ABSTRACT

Disclosed herein are quaternary ammonium compounds of the formula $R^1 R^2 R^3 N^+ —(CH_2)_m Y\ X_n^-$ wherein n is 1 or 2 depending on the valence of the cation; m is an integer from 1 to 6; Y is a group selected from Z, $—N^+R^1R^2R^3$, $—OH$, $—SOCl$, $—CH=CH_2$, $—O—R^4$, $—OSiR^5R^6R^7$, $—OC(O)R^8$, $—CN$, $—SO_4Q$, $—C\equiv CH$, epoxide, $—SR^{10}$, $—S(O_2)R^{11}$, $—S(O)R^{12}$,

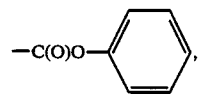

$SO_3Q$, $—Si(OR^{13})(OR^{14})—(OR^{15})$, $—OC(O)—(CH_2)_p—C(O)—O—(CH_2)_m—NR^1R^2R^3$, and $—NR^{16}R^{17}$ wherein m and p are integers, the R groups are hydrocarbyl, Q is H or alkali metal. They are useful as fungicides, herbicides, antiseptics and peroxygen bleach activators.

1 Claim, No Drawings

QUATERNARY AMMONIUM COMPOUNDS

BACKGROUND OF THE INVENTION

Quaternary ammonium compounds referred to as "quats", are nitrogen compounds having four groups bonded to a nitrogen atom by a covalent C—N bond. The nitrogen atom has a positive charge which requires a counter anion or a balancing negative charge in the quat compound itself. Such compounds are used as fungicides, algicides, bactericides, bleach activators and have many other well known uses. Quats can be easily made by reacting a compound having a covalent halogen atom with a tert-amine.

SUMMARY OF THE INVENTION

According to the present invention a new series of quats has been discovered having at least one of a group of functional radicals bonded to a quaternary nitrogen atom through a methylene group or a series of methylene groups. These new compounds have all the known uses of quaternary ammonium compounds. In addition some of the new quats are useful as hair conditioning agents, peroxygen bleach activators.

DESCRIPTION OF THE PREFERRED EMBODIMENTS

A preferred embodiment of the invention is a quaternary ammonium compound having the structure

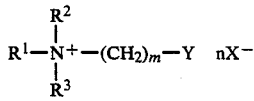

wherein $R^1$ is an alkyl group having 8–20 carbon atoms, $R^2$ is an alkyl containing 8–18 carbon atoms or is methyl, $R^3$ is methyl, Y is selected from the group consisting of

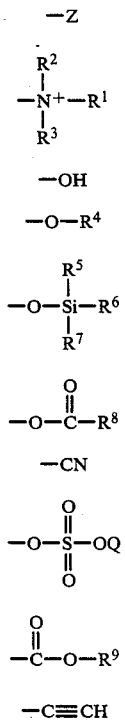

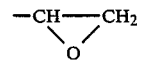
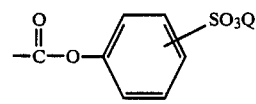
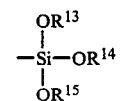
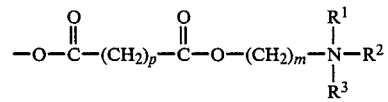
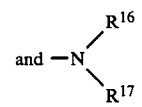

wherein m and p are integers from 1 to 6; n is 1 or is 2 when the cationic group has a valence of +2; X is a monovalent anion; $R^1$; $R^2$ and $R^3$ are as above; Z is a halogen; $R^4$, $R^8$, $R^9$, $R^{16}$ and $R^{17}$ are alkyls containing 1–6 carbon atoms; $R^5$, $R^6$, $R^7$, $R^{10}$, $R^{11}$, $R^{12}$, $R^{13}$, $R^{14}$ and $R^{15}$ are alkyl containing 1–10 carbon atoms or phenyl; and Q is an alkali metal or H.

For the sake of simplifying the following disclosure the chemical group:

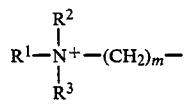

will be represented by the letter "A". Thus the first group of quats have the structure A—Z X⁻ wherein Z is a halogen such as chlorine, bromine, fluorine or iodine. The more preferred halogens are chlorine and bromine. Representative examples of these quats are:

decyl dimethyl 2-bromoethyl ammonium chloride;
dodecyl dimethyl 2-chloroethyl ammonium bromide;
didecyl methyl 3-bromoethyl ammonium chloride;
octadecyl dimethyl 4-chlorobutyl ammonium bromide;
hexadecyl dimethyl 2-bromoethyl ammonium bromide;
dioctyl methyl 6-bromohexyl ammonium bromide;
and the like.

More preferably $R^1$ is an alkyl containing 8–18 carbon atoms, $R^2$ is a $C_{8-18}$ alkyl or methyl, Z is chlorine or bromine and m is 2. Examples of these more preferred compounds are:

octyl dimethyl 2-chloroethyl ammonium chloride;
dioctyl methyl 2-bromoethyl ammonium bromide;
decyl dimethyl 2-bromoethyl ammonium bromide;

didecyl methyl 2-chloroethyl ammonium chloride;
dodecyl dimethyl 2-bromoethyl ammonium bromide;
didodecyl methyl 2-bromoethyl ammonium chloride;
tetradecyl dimethyl 2-chloroethyl ammonium chloride;
ditetradecyl methyl 2-bromoethyl ammonium bromide;
octadecyl dimethyl 2-chloroethyl ammonium chloride;
and the like.

Another group of new quats of the present invention are those having the structure $A-N^+R^1R^2R^3 \ 2X^-$. Examples of these compounds are:
N,N'-didodecyl-N,N,N',N'-tetramethyl ethylene diammonium dibromide;
N,N'-dioctadecyl-N,N,N',N'-tetramethyl-1,4-butane diammonium dichloride;
N,N'-dioctyl-N,N,N',N'-tetramethyl-1,6-hexane diammonium dibromide;
and the like.

As with the previous group, the more preferred compounds are those in which $R^1$ is a $C_{8-18}$ alkyl, $R^2$ is a $C_{8-18}$ alkyl or is methyl, m is 2 and X is chlorine or bromine. Some further examples of these are:
N,N'-dioctyl-N,N,N',N'-tetramethyl ethylene diammonium dibromide;
N,N'-didecyl-N,N,N',N'-tetramethyl ethylene diammonium dichloride;
N,N'-dioctadecyl-N,N,N',N'-tetramethyl ethylene diammonium dichloride;
N,N'-ditetradecyl-N,N,N',N'-tetramethyl ethylene diammonium dibromide;
N,N,N',N'-tetraoctyl-N,N'-dimethyl ethylene diammonium dibromide;
N,N,N',N'-tetradodecyl-N,N'-dimethyl ethylene diammonium dichloride;
and the like.

The foregoing two classes of compounds can made by reacting the appropriate tert-amine having the structure $NR^1R^2R^3$ with a dihaloalkane such as ethylene dibromide. The reaction is conducted at a temperature of about 20-100° C. using about 1 mole of tert-amine for each equivalent of halogen atom which is desired to be quaternerized. In other words to replace one halogen of the dihaloalkane 1 mole of tert-amine would be used whereas to replace both halogens of 1 mole of dihaloalkane, 2 moles of tert-amine would be used. Typical preparations of these compounds is shown in the following examples.

EXAMPLE 1

In a 5 liter 3-neck flask was placed 540.19 grams of decyldimethyl amine, 530.6 grams of ethylene dibromide and 1600 grams of ethyl acetate solvent. The mixture was stirred and heated under nitrogen for 24 hours. It was then cooled and diluted with isopropanol to cause precipitation of 0° C. of the product, N,N'-didecyl-N,N,N', N'-tetramethyl ethylene diammonium bromide.

EXAMPLE 2

In a 500 mL 3-neck flask was placed 72.1 grams of decyldimethyl amine, 35.42 grams of ethylene dibromide and 71.7 grams of ethyl acetate solvent. The mixture was stirred and heated under nitrogen at 90° C. and held at this temperature for 24 hours. The mixture was then cooled to 5° C. to precipitate decyl dimethyl 2-bromoethyl ammonium bromide which was recovered by filtration.

The next class of quats are those having the structure $A-OH \ X^-$. Some examples of these are:

didodecyl methyl 3-hydroxypropyl ammonium iodide;
octadecyl dimethyl 6-hydroxyhexyl ammonium fluoride;
and the like.

The more preferred compounds of this class are those in which $R^1$ is a $C_{8-18}$ alkyl, $R^2$ is a $C_{8-18}$ alkyl or methyl, m is 2 and X is chlorine or bromine. Examples of these preferred compounds are:
octyl dimethyl 2-hydroxyethyl ammonium bromide:
dioctyl methyl 2-hydroxyethyl ammonium chloride;
decyl dimethyl 2-hydroxyethyl ammonium chloride;
didecyl methyl 2-hydroxyethyl ammonium bromide;
dodecyl dimethyl 2-hydroxyethyl ammonium bromide;
didodecyl methyl 2-hydroxyethyl ammonium chloride;
tetradecyl dimethyl 2-hydroxyethyl ammonium chloride;
ditetradecyl methyl 2-hydroxyethyl ammonium bromide;
and the like.

These compounds can be readily made by reacting a halo alcohol, $X(CH_2)_m-OH$, with a tert-amine, $R^1R^2R^3N$. The reaction is usually conducted in an inert solvent under nitrogen at elevated temperatures for a period to essentially complete quaternerization of the amine which can be followed by disappearance of the amine group. The following example shows the preparation of the hydroxy alkyl quats.

EXAMPLE 3

In a reaction vessel was placed 17.37 grams of 2-bromo ethanol, 27.8 grams of dodecyl dimethyl amine and 41.3 grams of methylethyl ketone solvent. The mixture was stirred at reflux (approx. 78° C.) under nitrogen for about 4 hours. It was then cooled and a precipitate formed which was identified as dodecyl dimethyl 2-hydroxyethyl ammonium bromide. This product was recovered by filtration.

It was also discovered that the above reaction is catalyzed by the inclusion of a small amount of potassium iodide. As little as 0.05 up to 0.5 parts by weight or more of potassium iodide per 100 parts of tert-amine are effective. The following example shows this effect.

EXAMPLE 4

In a reaction vessel was placed 32.99 grams of dodecyl dimethyl amine, 0.03 grams KI, 0.3 mL water and 15 mL 2-chloro ethanol. While stirring under nitrogen, the mixture was heated to 100° C. After 3.5 hours, 30 mL of methylethyl ketone was added and after 5 hours 20 minutes an additional 70 mLs of methylethyl ketone was added to dissolve the quat that started to precipitate. The mixture was then cooled causing the product, dodecyl dimethyl 2-hydroxyethyl ammonium chloride to precipitate. Conversion was 90% based upon amine consumption.

Another class of quats of this invention can be represented by the formula

$$A-OR^4 \ X^-$$

wherein $R^4$ is an alkyl containing about 1–6 carbon atoms. Some examples of these compounds are:
octyl dimethyl 2-methoxyethyl ammonium bromide;
dioctadecyl methyl 2-butoxyethyl ammonium chloride;
didecyl methyl 2-hexoxyethyl ammonium fluoride;
tetradecyl dimethyl 3-methoxypropyl ammonium iodide;

octadecyl dimethyl 4-methoxybutyl ammonium bromide;
and the like.

More preferably $R^1$ is a $C_{8-18}$ alkyl, $R^2$ is a $C_{8-18}$ alkyl or a methyl group, m is 2 and X is chlorine or bromine. Examples of these preferred compounds are:
dioctyl methyl 2-methoxyethyl ammonium bromide;
didecyl methyl 2-ethoxyethyl ammonium chloride;
didodecyl methyl 2-propoxyethyl ammonium bromide;
dioctadecyl methyl 2-butoxyethyl ammonium chloride;
octyl dimethyl 2-methoxyethyl ammonium chloride;
decyl dimethyl 2-ethoxyethyl ammonium bromide;
dodecyl dimethyl 2-propoxyethyl ammonium iodide;
tetradecyl dimethyl 2-butoxyethyl ammonium fluoride;
octadecyl dimethyl 2-methoxyethyl ammonium bromide;
and the like.

These compounds can be made by reacting an appropriate alkoxy alkyl halide (e.g. $R^4$—O—$(CH_2)_m$—X) with a tert-amine (e.g. $R^1R^2R^3N$) at an elevated temperature to form the alkoxyalkyl quat. The following example shows a typical synthesis.

EXAMPLE 5

In a 2 liter 3-neck reaction flask was placed 212.3 grams tetradecyl dimethyl amine, 86.49 grams 2-methoxyethyl chloride and 425.45 grams para-dioxane solvent. The mixture was refluxed for 48 hours, cooled to crystallize the product and the white crystalline product recovered by filtration and identified as tetradecyl dimethyl 2-methoxyethyl ammonium chloride.

Another preferred class of new compounds can be represented by the structure

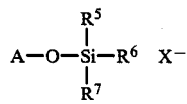

wherein $R^5$, $R^6$ and $R^7$ are alkyls containing about 1-10 carbon atoms or phenyl.

Representative examples of these compounds are:
octyl dimethyl trimethylsilyloxyethyl ammonium bromide;
dodecyl dimethyl triethylsilyloxypropyl ammonium chloride;
octadecyl dimethyl trihexylsilyloxybutyl ammonium iodide;
didecyl methyl trimethylsilyloxyhexyl ammonium fluoride;
octyl dimethyl triphenylsilyloxyethyl ammonium bromide;
didodecyl methyl triphenylsilyloxyethyl ammonium iodide;
octadecyl dimethyl triphenylsilyloxyethyl ammonium fluoride;
and the like.

The more preferred silyloxy quats are those in which $R^1$ is a $C_{8-18}$ alkyl, $R^2$ is a $C_{8-18}$ alkyl or a methyl group, $R^5$, $R^6$ and $R^7$ are alkyl, m is 2 and X is chlorine or bromine. Still more preferred are compounds in which $R^5$, $R^6$ and $R^7$ are methyl groups. Further examples of these are:
octyl dimethyl trimethylsilyloxyethyl ammonium chloride;
dioctyl methyl trimethylsilyloxyethyl ammonium bromide;
decyl dimethyl trimethylsilyloxyethyl ammonium bromide;
dodecyl dimethyl trimethylsilyloxyethyl ammonium chloride;
didodecyl methyl trimethylsilyloxyethyl ammonium bromide;
tetradecyl dimethyl trimethylsilyloxyethyl ammonium bromide;
dioctadecyl methyl trimethylsilyloxyethyl ammonium chloride;
and the like.

These compounds can be made by reacting a trialkyl chlorosilane such as $R^5R^6R^7SiCl$, with a trialkyl hydroxyalkyl ammonium halide, A—OH $X^-$. An inert solvent such as tetrahydrofuran, dimethoxyethane, diglyme, dioxane and the like can be used but is not required. The reaction should be conducted under nitrogen at from room temperature up to reflux. The following examples show the preparation of a typical silyloxy compound.

EXAMPLE 6

In a reaction vessel was placed 5.51 grams of dodecyl dimethyl 2-hydroxyethyl ammonium bromide. While stirring under nitrogen at room temperature, 50 mLs of trimethylchlorosilane was added. The temperature initially dropped from 25° to 20° C. Heat was applied and an exotherm was observed. The mixture was refluxed at 52° C. for 2 hours. The mixture was then cooled and a precipitate formed. The precipitate was removed by filtration, dried and analyzed as dodecyl dimethyl 2-trimethylsilyloxyethyl ammonium bromide.

Another group of compounds of the invention are those having the formula A—O—C(O)—$R^8$ $X^-$ wherein $R^8$ is an alkyl group containing about 1-6 carbon atoms. Representative examples of this embodiment are:
octyl dimethyl 2-acetyloxyethyl ammonium chloride;
octadecyl dimethyl 3-propionyloxypropyl ammonium iodide;
dioctyl methyl 3-acetyloxyhexyl ammonium bromide;
and the like.

In a more preferred embodiment, $R^1$ is a $C_{8-8}$ alkyl, $R^2$ is a $C_{8-18}$ alkyl or methyl group, $R^8$ is methyl, X is chlorine or bromine and m is 2. Some examples of these compounds are:
didecyl methyl 2-acetyloxyethyl ammonium bromide;
decyl dimethyl 2-acetyloxyethyl ammonium chloride;
octyl dimethyl 2-acetyloxyethyl ammonium chloride;
dioctyl methyl 2-acetyloxyethyl ammonium bromide;
dodecyl dimethyl 2-acetyloxyethyl ammonium bromide;
tetradecyl dimethyl 2-acetyloxyethyl ammonium bromide;
octadecyl dimethyl 2-acetyloxyethyl ammonium chloride.

These acyloxyalkyl quats can be made by reacting a haloalkyl alkanoate, X—$(CH_2)_m$—O—C(O)—$R^8$, with a tert-amine, $R^1R^2R^3N$. Preferably an inert solvent is used and the reaction is conducted under nitrogen at an elevated temperature up to reflux. The following examples illustrate how the compounds can be made.

EXAMPLE 7

In a glass reaction vessel under nitrogen was placed 78.25 grams of ethyl acetate solvent and 32.65 grams of 2-bromoethyl acetate. While stirring, 41.14 grams of dodecyl dimethyl amine was added dropwise. A slight exotherm was observed. Heat was applied and the temperature raised to reflux (ca. 89° C.) which was continued for 6 hours. The mixture was then cooled to −10° C. causing the product to precipitate. The product, dodecyl dimethyl acetyloxyethyl ammonium bromide, was recovered by filtration.

The above compounds can also be made by reacting an appropriate acyl halide, $R^8C(O)Cl$, with a hydroxyalkyl trialkyl quat, $R^1R^2R^3N^+(CH_2)_mOH\ X^-$. This method is shown in the following example.

EXAMPLE 8

In a reaction vessel was placed 13.14 grams of dodecyl dimethyl 2-hydroxyethyl ammonium bromide, 21.22 grams of acetone solvent and 4.72 grams of sodium carbonate. While stirring under nitrogen, 3.27 grams of acetyl chloride was added dropwise. Gas evolution occurred. The mixture was then refluxed (ca. 60° C.) for 6 hours. The solvent was removed under vacuum. The residue was extracted with isopropanol to dissolve the quat and the solution was filtered hot to remove sodium chloride and sodium carbonate. The filtrate was evaporated under vacuum leaving as the product dodecyl dimethyl acetyloxyethyl ammonium bromide.

Still another embodiment of the invention are compounds of the formula $A-CN\ X^-$. These can be exemplified by:
dioctyl methyl cyanomethyl ammonium bromide;
didecyl methyl 2-cyanopropyl ammonium chloride;
didodecyl methyl 5-cyanopentyl ammonium iodide;
octadecyl dimethyl 6-cyanohexyl ammonium fluoride;
and the like.

More preferably $R^1$ is a $C_{8-18}$ alkyl, $R^2$ is a $C_{8-18}$ alkyl or a methyl group, m is 2 and X is chlorine or bromine. These are illustrated by:
octyl dimethyl 2-cyanoethyl ammonium chloride;
decyl dimethyl 2-cyanoethyl ammonium bromide;
dodecyl dimethyl 2-cyanoethyl ammonium chloride;
tetradecyl dimethyl 2-cyanoethyl ammonium bromide;
octadecyl dimethyl 2-cyanoethyl ammonium bromide;
dioctyl methyl 2-cyanoethyl ammonium chloride;
didecyl methyl 2-cyanoethyl ammonium bromide;
and the like.

This class of quats can be made by reacting an appropriate haloalkyl nitrile, $X-(CH_2)_m-CN$, with a tert-amine, $R^1R^2R^3N$, in an inert solvent such as tetrahydrofuran, dioxane or diglyme and preferably under nitrogen and under substantially anhydrous conditions. The following example shows how the nitrile quats can be made.

EXAMPLE 9

In a reaction vessel was placed 130.5 grams of dioxane and 40.48 grams of dodecyl dimethyl amine. While stirring under nitrogen, 25.69 grams of 2-bromoethyl nitrile was added dropwise. An exotherm occurred raising the temperature to 40° C. and a white precipitate formed. The mixture was heated to reflux and held at reflux (ca. 95°–100° C.) for 2.5 hours. The mixture was then cooled and an additional 382.49 grams of para-dioxane was added. The product, dodecyl dimethyl 2-cyanoethyl ammonium bromide, precipitated and was recovered by filtration.

In another embodiment of the invention the novel quat has the formula

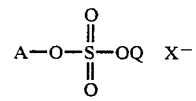

wherein Q is hydrogen or an alkali metal. When Q is an alkali metal, the alkali metal cation can precipitate the $X^-$ anion so that the resultant quat is internally neutralized as follows:

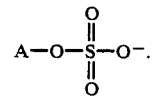

This internally neutralized sulfate quat is the equivalent of the same quat neutralized by an external anion and is within the scope of the invention. Some examples of these compounds are:
dioctyl methyl (2-hydrosulfatoethyl) ammonium bromide;
nonyl dimethyl (sodium 4-sulfatobutyl) ammonium chloride;
octadecyl dimethyl 2-hydrosulfatoethyl ammonium fluoride;
hexadecyl dimethyl 2-hydrosulfatobutyl ammonium bromide;
octyl dimethyl 2-sulfatoethyl ammonium bromide;
dodecyl dimethyl 2-sulfatoethyl ammonium chloride;
octadecyl dimethyl 3-sulfatopropyl ammonium bromide;
and the like.

In a preferred embodiment, $R^1$ is a $C_{8-18}$ alkyl, $R^2$ is a $C_{8-18}$ alkyl or a methyl group, m is 2 and X is chlorine or bromine. Representative examples of these compounds are:
octyl dimethyl 2hydrosulfatoethyl ammonium chloride;
dioctyl methyl 2-hydrosulfatoethyl ammonium bromide;
decyl dimethyl 2-hydrosulfatoethyl ammonium bromide;
decyl dimethyl 2-sulfatoethyl ammonium chloride;
dodecyl dimethyl 2-hydrosulfatoethyl ammonium chloride;
didodecyl methyl 2-hydrosulfatoethyl ammonium bromide;
tetradecyl dimethyl 2-hydrosulfatoethyl ammonium bromide;
octadecyl dimethyl 2-sulfatoethyl ammonium chloride;
and the like including the alkali metal salts.

One method of making these sulfate-substituted quats is to react chlorosulfonic acid, $ClSO_3H$, with the hydroxy quat $A-OH\ X^-$. This reaction is preferably conducted in an inert solvent under nitrogen at temperatures from 0° C. up to reflux. The following example illustrates the preparation of a sulfate quat.

EXAMPLE 10

In a reaction vessel was placed 29.45 grams of dodecyl dimethyl 2-hydroxyethyl ammonium bromide and 50 mLs of methylene chloride solvent. This was cooled to 5° C. and while stirring under nitrogen, 10.21 grams of chlorosulfonic acid was added dropwise over 15 minutes at 5°–10° C. Then 4.75 grams of sodium carbonate was added to neutralize the mixture and the orange solution was filtered. The methylene chloride was evaporated from the filtrate under vacuum leaving as the product a light tan solid identified as dodecyl dimethyl 2-sulfatoethyl ammonium bromide.

The sulfato quat can also be made by the direct sulfonation of the hydroxyalkyl quat, A—OH X$^-$, with SO$_3$. This is shown in the following example.

EXAMPLE 11

In a reaction vessel was placed 8.15 grams of dodecyldimethyl 2-hydroxyethyl ammonium bromide and 25 mLs of methylene chloride. This solution was stirred under nitrogen and cooled to 10° C. Then, 2.62 grams of liquid SO$_3$ was added dropwise at 10°–15° C. Unreacted SO$_3$ was then sparged from the flask with nitrogen. Sufficient sodium carbonate was added to neutralize acidity and the mixture was filtered. The filtrate was evaporated under vacuum leaving as the product dodecyl dimethyl sulfatoethyl ammonium bromide.

Another class of compounds of the invention are those having the formula A—C(O)—O—R$^9$ X$^-$ wherein R$^9$ is an alkyl containing from 1 to about 6 carbon atoms or a phenyl group. Representative examples of these compounds are:
octyl dimethyl (2-acetic acid hexyl ester) ammonium bromide;
decyl dimethyl (3-propionic acid phenyl ester) ammonium iodide;
octyl dimethyl (4-butyric acid hexyl ester) ammonium chloride;
hexadecyl dimethyl (6-hexanoic acid butyl ester) ammonium fluoride;
and the like.

The more preferred compounds are those in which R$^1$ is a C$_{8-18}$ alkyl, R$^2$ is a C$_{8-18}$ alkyl or a methyl group, m is 1 or 2, and X is chlorine or bromine. Some examples of these preferred compounds are:
octyl dimethyl (2-acetic acid methyl ester) ammonium bromide;
decyl dimethyl (3-propionic acid octyl ester) ammonium chloride;
dodecyl dimethyl (2-acetic acid phenyl ester) ammonium bromide;
tetradecyl dimethyl (3-propionic acid butyl ester) ammonium chloride;
and the like.

These compounds can be made by reacting an appropriate haloalkanoate ester, X—(CH$_2$)$_m$—C(O)—OR$^9$, with a trialkyl amine, R$^1$R$^2$R$^3$N. The reaction is conducted in an inert solvent at an elevated temperature up to reflux. The following example illustrates the way these compounds are made.

EXAMPLE 12

In a reaction flask was placed 8.16 grams of methyl 3-bromopropionate and 20 mL methylethyl ketone. To this was added 11.26 grams of tetradecyl dimethyl amine and the mixture was refluxed for 6 hours. The reaction mixture was then cooled and the product, tetradecyl dimethyl (3-propionic acid methyl ester) ammonium bromide precipitated.

The ester quat can also be made by esterification of the appropriate betaine.

EXAMPLE 13

In a reaction flask was placed 20 grams of dodecyldimethyl betaine, 1.83 grams of phenol, 20 mLs of toluene and 1 mL of conc. HCl. This was heated to reflux and water was removed using a Dean-Stark water trap. Temperature gradually rose to 110° C. at which time no more water came off. After 4 hours the mixture was cooled and the product dodecyldimethyl (2-acetic acid phenyl ester) ammonium chloride precipitated and was recovered by filtration.

A still further group of compounds of the invention are the alkyne quats having the structure A—C≡CH. In this application the compounds will be named as alkyne substituted quaternary ammonium compounds such that the compound (CH$_3$)$_3$N$^+$—CH$_2$—C≡CH Cl$^-$ is named trimethyl 3-(1-propyne) ammonium chloride. Other examples of these acetylenic quats are:
octyl dimethyl 4-(1-butyne) ammonium iodide;
octadecyl dimethyl 6-(1-hexyne) ammonium fluoride;
didodecyl methyl 3-(1-propyne) ammonium chloride;
and the like.

The more preferred compounds of this class are those wherein R$^1$ is a C$_{8-18}$ alkyl, R$^2$ is a C$_{8-18}$ alkyl or a methyl group, m is 1 and X is chlorine or bromine. Examples of these more preferred acetylenic quats are:
octyl dimethyl 3-(1-propyne) ammonium chloride;
decyl dimethyl 3-(1-propyne) ammonium bromide;
dodecyl dimethyl 3-(1-propyne) ammonium chloride;
tetradecyl dimethyl 3-(1-propyne) ammonium bromide;
octadecyl dimethyl 3-(1-propyne) ammonium chloride;
dioctyl methyl 3-(1-propyne) ammonium chloride;
didodecyl methyl 3-(1-propyne) ammonium bromide;
and the like.

The acetylenic quats can be made by reacting the appropriate haloalkyne, X—(CH$_2$)$_m$—C≡CH, with the appropriate tert-amine, R$^1$R$^2$R$^3$N. The reaction does not require a solvent although an inert solvent can be used. The following example illustrates how the acetylenic quats can be made.

EXAMPLE 14

In a reaction flask was placed 64.28 grams of octyl dimethyl amine and 90.17 grams of methylethyl ketone. With stirring and under a nitrogen atmosphere, 30.76 grams of propargyl chloride was added dropwise over a 30 minute period. The mixture was then heated to reflux (ca. 85° C.) and held at reflux for 1 hour. It was then cooled and the product, octyl dimethyl 3-(1-propyne) ammonium chloride separated as a dark gold liquid.

Another useful quat of the invention is represented by the formula

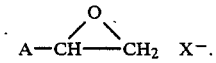

These are referred to as epoxy quats. Some representative examples are:
octyl dimethyl 2,3-epoxypropyl ammonium chloride;
octadecyl dimethyl 5,6-epoxyhexyl ammonium bromide;
didecyl methyl 3,4-epoxybutyl ammonium iodide;
dodecyl dimethyl 2,3-epoxypropyl ammonium fluoride;
and the like.

In a more preferred embodiment R$^1$ is a C$_{8-18}$ alkyl, R$^2$ is a C$_{8-18}$ alkyl or a methyl group, m is 1 and X is chlorine or bromine. Some of these more preferred epoxy quats are:
octyl dimethyl (2,3-epoxypropyl) ammonium chloride;

decyl dimethyl (2,3-epoxypropyl) ammonium bromide;
dodecyl dimethyl (2,3-epoxypropyl) ammonium chloride;
tetradecyl dimethyl (2,3-epoxypropyl) ammonium bromide;
octadecyl dimethyl (2,3-epoxypropyl) ammonium chloride;
dioctyl methyl (2,3-epoxypropyl) ammonium chloride;
didecyl methyl (2,3-epoxypropyl) ammonium bromide;
ditetradecyl methyl (2,3-epoxypropyl) ammonium chloride;
dihexadecyl methyl (2,3-epoxypropyl) ammonium bromide;
and the like.

The epoxy quats can be made by reacting an epoxy halide,

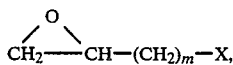

with a tert-amine, $R^1R^2R^3N$. The reaction is run in an inert solvent such as tetrahydrofuran, dioxane, dimethoxyethane and the like and under a nitrogen atmosphere at 20° C. up to reflux and preferably under substantially anhydrous conditions. The following example shows how the epoxy quats can be made.

EXAMPLE 15

In a reaction flask was placed 12.4 grams of epibromohydrin, 18.73 grams of dodecyldimethyl amine and 21.34 grams of para-dioxane solvent. This was stirred and heated under nitrogen to reflux (ca. 90° C.). After 6 hours at reflux the mixture was cooled. Solvent removed under vacuum to afford product, dodecyl dimethyl (2,3-epoxypropyl) ammonium bromide as a clear gel.

Another embodiment of the invention is an alkylthio quat. These are compounds having the formula $A-S-R^{10}X^-$ wherein $R^{10}$ is an alkyl containing 1 to about 10 carbon atoms or a phenyl group. Some examples of these compounds are:
octyl dimethyl methylthioethyl ammonium chloride;
octadecyl dimethyl butylthioethyl ammonium bromide;
octadecyl dimethyl hexylthiobutyl ammonium iodide;
hexadecyl dimethyl decylthiohexyl ammonium fluoride;
dodecyl dimethyl ethylthiopentyl ammonium bromide;
octyl dimethyl phenylthioethyl ammonium bromide;
didodecyl methyl phenylthiobutyl ammonium iodide;
and the like.

The more preferred alkylthio quats of this embodiment are those in which $R^1$ is a $C_{8-18}$ alkyl, $R^2$ is a $C_{8-18}$ alkyl or a methyl group, $R^{10}$ is alkyl, m is 1 and X is chlorine or bromine. Some examples of these more preferred compounds are:
octyl dimethyl methylthiomethyl ammonium bromide;
decyl dimethyl ethylthiomethyl ammonium chloride;
dodecyl dimethyl butylthiomethyl ammonium bromide;
tetradecyl dimethyl decylthiomethyl ammonium chloride;
dioctyl methyl methylthiomethyl ammonium chloride;
didecyl methyl ethylthiomethyl ammonium bromide;
didodecyl methyl butylthiomethyl ammonium chloride;
ditetradecyl methyl decylthiomethyl ammonium bromide;
and the like.

These alkylthio quats can be made by reacting an alkylthio alkyl halide, $R^{10}-S-(CH_2)_m-X$, with a tert-amine, $R^1R^2R^3N$, in an inert solvent at an elevated temperature of about 50° C. up to reflux. The reaction is preferably maintained under nitrogen. Some of the alkylthio alkyl halides used in the preparation are stench compounds so due caution should be maintained. The preparation of a typical alkylthio quat is shown in the following example.

EXAMPLE 16

In a reaction vessel was placed 99.9 grams of methylethyl ketone, 70.02 grams of tetradecyl dimethyl amine and 30.9 grams of methylthiomethylchloride. The mixture was stirred and heated under nitrogen to reflux (ca. 90° C.) and held at reflux for 6 hours. It was then cooled and the product, tetradecyl dimethyl methylthiomethyl ammonium chloride precipitated as a yellow-white solid and was recovered by filtration.

The following example shows the preparation of an alkylthio quat without the use of a solvent.

EXAMPLE 17

In a glass reaction vessel was placed 86.52 grams of didecyl methyl amine. The amine was stirred under nitrogen and 29.07 grams of methylthiomethylchloride was added dropwise over 5 minutes. The mixture was then heated to 100° C. and stirred at 100° C. for 6 hours. On cooling the product, didecyl methyl methylthiomethyl ammonium chloride solidified.

A still further embodiment of the invention are the sulfone quats having the structure

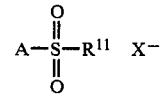

wherein $R^{11}$ is an alkyl containing 1 to about 10 carbon atoms or a phenyl group. Some examples of these compounds are:
decyl dimethyl methylsulfonomethyl ammonium chloride;
hexadecyl dimethyl butylsulfonoethyl ammonium bromide;
octadecyl dimethyl hexylsulfonobutyl ammonium fluoride;
dioctyl dimethyl decylsulfonohexyl ammonium iodide;
octyl dimethyl phenylsulfonatoethyl ammonium chloride;
dodecyl dimethyl phenylsulfonatopropyl ammonium bromide;
dioctyl methyl phenylsulfonatomethyl ammonium iodide;
and the like.

Of the above sulfone quats, the more preferred are those in which $R^1$ is a $C_{8-18}$ alkyl, $R^2$ is a $C_{8-18}$ alkyl or a methyl group, $R^{11}$ is alkyl, m is 1 and X is chlorine or bromine. Some examples of these compounds are:
octyl dimethyl methylsulfonomethyl ammonium chloride;
decyl dimethyl ethylsulfonomethyl ammonium bromide;
dodecyl dimethyl butylsulfonomethyl ammonium chloride;
tetradecyl dimethyl decylsulfonomethyl ammonium bromide;
octadecyl dimethyl methylsulfonomethyl ammonium chloride;

dioctyl methyl methylsulfonomethyl ammonium chloride;
didecyl methyl propylsulfonomethyl ammonium bromide;
didodecyl methyl hexylsulfonomethyl ammonium chloride;
ditetradecyl methyl octylsulfonomethyl ammonium bromide;
and the like.

The new compounds can be made by oxidizing the previous alkylthio quats using aqueous hydrogen peroxide. Care should be taken so that a large amount of unreacted hydrogen peroxide is not allowed to buildup in the reaction mixture. The following example shows the preparation of a typical sulfone substituted quat.

EXAMPLE 18

In a reaction vessel was placed 20.5 grams of the didecyl methyl methylthiomethyl ammonium chloride made in Example 17. This was heated to 60° C. to melt the quat and then 10.5 grams of 50% aqueous hydrogen peroxide was added dropwise over a 1 hour period with vigorous stirring. An exothermic reaction occurred. The reaction was then heated to 75° C. and held at this temperature for 4 hours forming a pale yellow liquid. On cooling the liquid gelled. Infrared confirmed the compound as being didecyl methyl methylsulfonomethyl chloride.

Another embodiment of the invention can be represented by sulfoxide substituted quats which have the formula

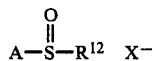

wherein $R^{12}$ is an alkyl containing about 1 to 10 carbon atoms or a phenyl group. These compounds can be exemplified by the following:
octyl dimethyl butylsulfoxomethyl ammonium chloride;
dodecyl dimethyl decylsulfoxoethyl ammonium bromide;
dioctyl methyl octylsulfoxomethyl ammonium fluoride;
octadecyl dimethyl phenylsulfoxomethyl ammonium bromide;
and the like.

In a more preferred embodiment of the sulfoxide quat, $R^1$ is a $C_{8-18}$ alkyl, $R^2$ is a $C_{8-18}$ alkyl or a methyl group, $R^{12}$ is alkyl, m is 1 and X is chlorine or bromine. Representative examples of this more preferred class of compounds are:
octyl dimethyl methylsulfoxomethyl ammonium chloride;
decyl dimethyl ethylsulfoxomethyl ammonium bromide;
dodecyl dimethyl butylsulfoxomethyl ammonium chloride;
tetradecyl dimethyl decylsulfoxomethyl ammonium bromide;
dioctyl methyl methylsulfoxomethyl ammonium bromide;
didecyl methyl ethylsulfoxomethyl ammonium chloride;
didodecyl methyl butylsulfoxomethyl ammonium bromide;
ditetradecyl methyl decylsulfoxomethyl ammonium chloride;
and the like.

The sulfoxide quats can be made by the oxidation of the alkylthio quats using the proper stoichiometry to oxidize the sulfur to the tetravalent state. The preparation of a sulfoxide quat is shown in the following example.

EXAMPLE 19

In a glass reaction flask was placed 21.95 grams of the didecyl methyl methylthiomethyl ammonium chloride from Example 17. This was warmed to 60° C. to melt the quat and 4.03 grams of 50% aqueous hydrogen peroxide was added dropwise over 8 minutes at 60° C. with vigorous stirring. The mixture was then heated to 75° C. and held at 75° C. for 2 hours. On cooling the product, didecyl methyl methylsulfoxomethyl ammonium chloride was recovered as a brown liquid.

A still further embodiment of the invention is an acyloxybenzene sulfonate (AOBS) quat of the structure

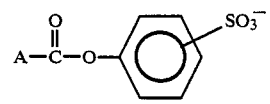

In this embodiment $X^-$ is not shown because upon neutralization of the sulfonic acid group the negative charge resides on the resulting sulfonate substituent making it unnecessary to include the $X^-$ anion. Representative examples of these compounds are:
3-(octyl dimethyl ammonium)propionyloxybenzene sulfonate;
4-(dodecyl dimethyl ammonium)butyryloxybenzene sulfonate;
2-(octadecyl dimethyl ammonium)acetyloxybenzene sulfonate;
6-(decyl dimethyl ammonium)hexanoyloxybenzene sulfonate;
and the like.

In a more preferred embodiment of the AOBS quat, $R^1$ is a $C_{8-18}$ alkyl, $R^2$ is a $C_{8-18}$ alkyl or a methyl group, and m is 2. Examples of this preferred class are:
3-(octyl dimethyl ammonium)propionyloxybenzenesulfonate;
3-(decyl dimethyl ammonium)propionyloxybenzenesulfonate;
3-(dodecyl dimethyl ammonium)propionyloxybenzenesulfonate;
3-(tetradecyl dimethyl ammonium)propionyloxybenzenesulfonate;
3-(tetradecyl dimethyl ammonium)propionyloxybenzenesulfonate;
3-(dioctyl methyl ammonium)propionyloxybenzenesulfonate;
3-(didecyl methyl ammonium)propionyloxybenzenesulfonate;
3-(didodecyl methyl ammonium)propionyloxybenzenesulfonate;
3-(ditetradecyl methyl ammonium)propionyloxybenzenesulfonate;
and the like.

In addition to the usual fungicide algicide and bactericidal properties of the other quats of this invention, the AOBS quats are also useful as bleach activators for peroxygen bleaching compounds such as sodium perborate.

The AOBS quats can be made by reacting a haloalkonyloxybenzenesulfonate alkali metal salt,

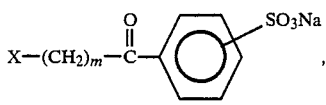

with a tert-amine, $R^1R^2R^3N$. The reaction is conducted in a solvent such as methylethyl ketone, tetrahydrofuran, dioxane and the like at an elevated temperature up to reflux and under a nitrogen atmosphere. The following example shows how the AOBS quats can be made.

EXAMPLE 20

Initially, 3-bromopropionyloxybenzenesulfonate sodium salt was made by reacting 3-bromopropionylchloride with the sodium salt of parahydroxybenzene sulfonic acid in methylethyl ketone at reflux. The solid intermediate precipitated on cooling.

In a glass reaction flask was placed 20.11 grams of the above sodium salt, 13.21 grams of dodecyl dimethyl amine and 100 mLs methylethyl ketone. This was refluxed under nitrogen for 6 hours. The mixture was then cooled and the product was recovered by removal of solvent under vacuum and identified as dodecyl dimethyl propionylbenzenesulfonate.

Another embodiment of the invention is a siloxane quat having the formula

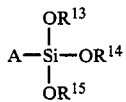

wherein $R^{13}$, $R^{14}$ and $R^{15}$ are alkyls containing 1-10 carbon atoms or are phenyl groups. Some examples of these compounds are:
3-(octyl dimethyl ammonium)propyl trimethoxysilane chloride;
4-(octadecyl dimethyl ammonium)butyl triethoxysilane bromide;
6-(octyl dimethyl ammonium)hexyl tridecyloxysilane iodide;
4-(eicosyl dimethyl ammonium)butyl tributoxysilane fluoride;
and the like.

In a more preferred embodiment $R^1$ is an alkyl group containing 8-18 carbon atoms, $R^2$ is an alkyl containing 8-18 carbon atoms or a methyl group, $R^3$, $R^{13}$, $R^{14}$ and $R^{15}$ are methyl, m is 2 or 3 and X is chlorine or bromine. Some examples of these more preferred compounds are:
2-(octyl dimethyl ammonium)ethyl trimethoxysilane chloride;
3-(decyl dimethyl ammonium)propyl trimethoxysilane bromide;
2-(dodecyl dimethyl ammonium)ethyl trimethoxysilane chloride;
3-(tetradecyloxy dimethyl ammonium)propyl trimethoxysilane bromide;
2-(dioctyl methyl ammonium)ethyl trimethoxysilane chloride;
3-(didecyl methyl ammonium)propyl trimethoxysilane bromide;
2-(ditetradecyl methyl ammonium)ethyl trimethoxysilane chloride;
and the like.

The silane-substituted quats can be made by reacting the appropriate haloalkyl trialkoxy silane,

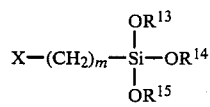

with a tert-amine, $R^1R^2R^3N$. The reaction is conducted at an elevated temperature of about 50°–100° C. and under nitrogen. The following example shows how these compounds can be made.

EXAMPLE 21

In a reaction vessel was placed 12.82 grams of 3-chloropropyl trimethoxysilane and 15.6 grams of tetradecyldimethyl amine. The mixture was stirred under nitrogen and heated to 95° C. After 2 hours at 95° C., a few crystals of KI were added. After 5 hours at 95° C. the product that formed was found to be 3-(tetradecyl dimethyl ammonium)propyl trimethoxysilane chloride.

A small amount of this product was placed on a glass surface and rubbed to provide a water-repellant brilliant finish. A portion was also rubbed on a metal surface providing a highly polished finish.

Another embodiment of the invention is the group of diquats which have the formula

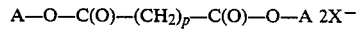

wherein p is an integer from 0 to 6. Examples of these compounds are:
di-(octyl dimethyl ammonium ethyl)ocalate dibromide;
di-(didecyl methyl ammonium ethyl)succinate dichloride;
di-(eicosyl dimethyl ammonium ethyl)malonate diiodide;
di-(hexadecyl dimethyl ammonium propyl)glutarate difluoride;
di-(dinonyl methyl ammonium butyl)suberate dibromide;
and the like.

In a more preferred embodiment, $R^1$ is an alkyl containing 8-18 carbon atoms, $R^2$ is an alkyl containing 8-18 carbon atoms or the methyl group, m is 2 or 3, p is 2-4 and X is chlorine or bromine. Some examples of these compounds are:
di-(octyl dimethyl ammonium ethyl)succinate dichloride;
di-(decyl dimethyl ammonium propyl)glutarate dibromide;
di-(dodecyl dimethyl ammonium ethyl)adipate dichloride;
di-(tetradecyl dimethyl ammonium propyl)succinate dibromide;
di-(octadecyl dimethyl ammonium ethyl)succinate dichloride;
di-(dioctyl methyl ammonium ethyl)succinate dichloride;
di-(didecyl methyl ammonium propyl)glutarate dibromide;
di-(didodecyl methyl ammonium ethyl)adipate dichloride;
di-(ditetradecyl methyl ammonium propyl)succinate dibromide.

These compounds can be made by reacting the appropriate hydroxy alkyl quat, A—$(CH_2)_m$—OH, with a diacyl halide, $XC(O)$—$(CH_2)_p$—$C(O)X$ in an inert solvent at 30° up to reflux, preferably under nitrogen. The following example shows a typical preparation.

EXAMPLE 22

Initially a hydroxyethyl quat was made by reacting 100 grams of dioctyl methyl amine with 42 mLs of 2-chloroethanol in 200 grams of methylethyl ketone solvent at reflux for 5 hours to obtain a methylethyl ketone solution of dioctyl methyl hydroxyethyl ammonium chloride. To this was added dropwise, 59.04 grams of glutaryl dichloride over a 1 hour period while sparging the mixture with nitrogen. This was held at reflux (90° C.) for 30 minutes to give a brown solution of di(dioctyl methyl ammonium ethyl)glutarate dichloride which could be recovered by evaporation of the methylethyl ketone under vacuum.

We claim:
1. Tetradecyl dimethyl 2-methoxyethyl ammonium chloride.

* * * * *